US008213015B2

(12) United States Patent
Kraizcek et al.

(10) Patent No.: US 8,213,015 B2
(45) Date of Patent: Jul. 3, 2012

(54) INTEGRATED FLOW CELL WITH SEMICONDUCTOR OXIDE TUBING

(75) Inventors: Karsten Kraizcek, Waldbronn (DE); Beno Mueller, Ettlingen (DE); Timothy Beerling, Los Angeles, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 562 days.

(21) Appl. No.: 12/237,398

(22) Filed: Sep. 25, 2008

(65) Prior Publication Data

US 2010/0277722 A1     Nov. 4, 2010

(51) Int. Cl.
*G01N 21/00*     (2006.01)
(52) U.S. Cl. ......... 356/440; 356/436; 356/445; 356/246
(58) Field of Classification Search .......... 356/244, 356/246, 436, 440, 73; 422/82.05, 82.09; 250/428–438; 435/288.5; 73/36, 61, 69, 73/64, 43
See application file for complete search history.

(56) References Cited

U.S. PATENT DOCUMENTS

| | | | |
|---|---|---|---|
| 5,153,679 A | 10/1992 | Gilby | |
| 5,184,192 A | 2/1993 | Gilby | |
| 5,599,503 A * | 2/1997 | Manz et al. | 422/82.05 |
| 2002/0072243 A1 * | 6/2002 | Craighead et al. | 438/745 |
| 2003/0076491 A1 | 4/2003 | Mueller | |
| 2005/0128367 A1 * | 6/2005 | Hoke et al. | 349/1 |
| 2007/0097361 A1 | 5/2007 | Beigel | |
| 2007/0132229 A1 | 6/2007 | Mueller | |
| 2007/0132230 A1 | 6/2007 | Mueller | |
| 2007/0132241 A1 | 6/2007 | Mueller | |
| 2007/0172940 A9 * | 7/2007 | Manalis et al. | 435/287.2 |
| 2008/0079942 A1 | 4/2008 | Buettner | |

FOREIGN PATENT DOCUMENTS

WO     2007009492 A1     1/2007

OTHER PUBLICATIONS

Daniel Sobek, A Microfabricated Flow Chamber for Optical Measurements in Fluids, 1993, pp. 219-224.*
K. Mogensen, J. El-Ali, A. Wolff, J. Kutter, "Integration of polymer waveguides for optical detection in microfabricated chemical analysis systems", Applied Optics, vol. 42, No. 19, 2003, pp. 4072 to 4079.

* cited by examiner

*Primary Examiner* — Tarifur Chowdhury
*Assistant Examiner* — Michael P Lapage

(57) ABSTRACT

An integrated flow cell, the flow cell comprising a semiconductor substrate, and a fluidic conduit having an at least partially transparent semiconductor oxide tubing, wherein the semiconductor oxide tubing is formed with the semiconductor substrate.

19 Claims, 10 Drawing Sheets

INTEGRATED FLOW CELL WITH SEMICONDUCTOR OXIDE TUBING

BACKGROUND ART

The present invention relates to a flow cell.

In liquid chromatography, a fluidic analyte may be pumped through conduits and a column comprising a material which is capable of separating different components of the fluidic analyte. Such a material, so-called beads which may comprise silica gel, may be filled into a column tube which may be connected to other elements (like a control unit, containers including sample and/or buffers) by conduits.

When a fluidic sample is pumped through the column tube, it is separated into different fractions. The separated fluid may be pumped in a flow cell in which the different components are identified on the basis of an optical detection mechanism.

U.S. Pat. No. 5,153,679 discloses an apparatus for measuring light absorbance in a liquid sample which includes a light source for directing light into a sample cell, a cylindrical sample cell, a light detector for measuring intensity of light emitted from the cell and focusing means for forming a tapered light beam to pass through the sample cell. The tapered light beam can be either a diverging beam or a converging beam through the cell. When the light beam is a diverging beam, a masking means is positioned downstream of the cell to assure that any light striking the cell wall is not directed to the light detector.

Further conventional flow cells are disclosed in US 2003/0076491, US 2008/0079942, US 2007/0097361, US 2007/0132230, US 2007/0132241, US 2007/0132229, and WO 2007/009492.

K. Mogensen, J. El-Ali, A. Wolff, J. Kutter, "Integration of polymer waveguides for optical detection in microfabricated chemical analysis systems", Applied Optics, Vol. 42, No. 19, 2003, pp. 4072 to 4079, discloses multimode polymer waveguides and fiber-to-waveguide couplers integrated with microfluidic channels by use of a single-mask-step procedure, which ensures self-alignment between the optics and the fluidics.

Conventional flow cells may be complex in manufacture. Typical dimensions of the flow path of a conventional HPLC-UV/Vis absorption cell, as stated in U.S. Pat. No. 5,153,679, are 10 mm length, 1 mm diameter and about 8 micro liters volume. The flow path is not always cylindrical, it may also have a conical shape, for instance a taper cell. The dimensions of these cells often require special machining methods in manufacturing, for example such as electric discharge machining, which has limited geometrical accuracy. But in order to avoid the undesired refractive index effects, as described in the source above, small tolerances are required. Spark eroding also can introduce unwanted electrode atoms, for example copper atoms, into the cell body material. The copper atoms can lead to spurious signals when the cell is used with extremely sensitive detectors, for example mass spectrometers.

To achieve better chromatographic resolution in HPLC, capillary LC or CE, the cell volumes have to become smaller and hence their inside diameters. In U.S. Pat. No. 5,184,192 A, liquid waveguide cells with typical inside diameters in the range from 0.5 mm to 0.05 mm are described. The manufacturing of these type of cells with such small geometries and reflecting walls require special and complex procedures. Coatings of fluoropolymers like Teflon AF are used to achieve total internal reflection. The coatings are manufactured by series of filling the cell with a Teflon AF solution followed by drying and baking processes or by complex alternative methods.

DISCLOSURE

It is an object of the invention to provide a flow cell which can be manufactured with reasonable effort (particularly flow cells with very low volumes, for instance <1 micro liter). The object is solved by the independent claims. Further embodiments are shown by the dependent claims.

According to an exemplary embodiment of the present invention, an at least partially (for instance monolithically) integrated flow cell is provided, the flow cell comprising a semiconductor substrate, and a fluidic conduit having an at least partially transparent semiconductor oxide tubing, wherein the semiconductor oxide tubing is (for instance monolithically) formed with the semiconductor substrate.

According to another exemplary embodiment, a fluidic device for measuring a fluidic sample is provided, the fluidic device comprising a processing unit adapted for processing the fluidic sample, and a flow cell having the above mentioned features in fluid communication with the processing unit for receiving the processed fluidic sample from the processing unit.

According to still another exemplary embodiment, a method of manufacturing an (for instance monolithically) integrated flow cell is provided, the method comprising providing a semiconductor substrate, and forming a fluidic conduit having an at least partially transparent semiconductor oxide tubing, wherein the semiconductor oxide tubing is (for instance monolithically) formed with the semiconductor substrate.

According to an exemplary embodiment, a flow cell for a fluidic device may be provided which flow cell can be manufactured in (for instance monolithically) integrated semiconductor technology. Thus, it is possible that the flow cell is at least partially formed from a common block of semiconductive material such as a silicon wafer. Such an integrated flow cell may comprise a fluidic conduit such as a channel which may be delimited by an optically transparent tubing manufacturable of a semiconductor oxide material which may originate from a part of the material of the semiconductor substrate in which the flow cell is (for instance monolithically) integrated. Thus, material of the semiconductor substrate may be chemically converted to produce a for instance optically transparent fluidic conduit tubing, or a patterned surface of the semiconductor material may be used as a template for growing a corresponding semiconductor oxide tubing. Thus, with reasonable effort, it is possible to manufacture a miniaturized flow cell which can be adapted to accommodate a fluidic sample which can be conducted through the semiconductor oxide tubing for instance for optical detection purposes. While the fluidic sample flows through the semiconductor oxide tubing, an optical detection along the longitudinal axis of the semiconductor oxide tubing may be made possible, in a similar manner as known by conventional flow cells. Such an integrated flow cell may be implemented in a fluid separation apparatus such as a liquid chromatography apparatus and may allow to reduce a size such a detection cell while being simultaneously capable of withstanding high pressures.

In the following, further exemplary embodiments of the flow cell will be explained. However, these embodiments also apply to the fluidic device and the method.

The semiconductor substrate may be a silicon substrate and the semiconductor oxide tubing may be a silicon oxide tubing. Using the material configuration silicon/silicon oxide ($SiO_2$) may be particularly advantageous for the flow cell, since silicon technology is a well established technology and silicon oxide has the advantageous property of being optically transparent and chemically inert, thereby making the material appropriate for optical flow cell applications. Moreover, it is possible to convert silicon material into silicon oxide material, for instance by thermal oxidation, or to use the silicon material as a template for growing silicon oxide thereon. However, alternatively, other group-IV semiconductors may be used, such as germanium. It is also possible that group-III group-V semiconductors are used for this purpose, for instance gallium arsenide.

The semiconductor substrate may be a monocrystalline substrate. The term "monocrystalline" may denote a single crystal or crystalline solid in which the crystal lattice of the entire sample is continuous, basically without grain boundaries. The opposite of a single crystal sample is an amorphous structure where the atomic position is limited to short range order only. Using a monocrystalline substrate may allow to make use of a possible asymmetry of the mechanical stability of such a substrate along the different crystal axis. For instance, this may allow to anisotropically etch recesses in a monocrystalline substrate to thereby form the geometrical basis for subsequently forming the tubing.

The semiconductor oxide tubing may have a rectangular cross section. Thus, the fluid flow may be through an essentially rectangular tubing which allows to manufacture the flow cell with reasonable effort. A rectangular cross section may be the result of the formation of a rectangular trench in two substrates to be bonded.

Alternatively, the semiconductor oxide tubing may have a hexagonal cross section. Such a hexagonal cross section may be formed making use of the crystal anisotropy of a monocrystalline silicon substrate used as a basis for the flow cell. It is possible to etch a trapezoidal recess in a surface of such a monocrystalline silicon substrate. Bonding two substrates processed in the described way in a manner that the two trapezoidal recesses are aligned to one another allows to manufacture such a hexagonal cross section.

The semiconductor oxide tubing may have a tubular section and may have a planar section, the tubular section delimiting the fluidic conduit and the planar section defining a beginning and an end of the fluidic conduit in the semiconductor substrate. Thus, the planar sections may define transparent end plates through which an optical detection may be performed.

The semiconductor oxide tubing may be optically transparent. In other words, it is possible that the semiconductor oxide tubing is transparent for electromagnetic radiation in the visible range, i.e. between 400 nm and 800 nm. Additionally or alternatively, it is possible that the semiconductor oxide tubing is optically transparent for ultraviolet radiation, infrared radiation, or any other wavelength range of electromagnetic radiation used for detection purposes.

The semiconductor oxide tubing may be adapted so that an electromagnetic radiation beam propagating through the fluidic conduit is totally reflected at the semiconductor oxide tubing (for instance at an inner or an outer surface thereof). Total reflection may be advantageous, because this may guarantee that basically all rays used for detection purposes remain within the detection cell and contribute to the detection signal. Total reflection may be denoted as a phenomenon that photons entirely reflect off the surface when the photons propagate from a medium of a high index of refraction towards a medium of a lower index of refraction. For example, total reflection may occur when passing light from glass to air, but not when passing light from air to glass.

A surface of the semiconductor oxide tubing may be lined with a reflection layer adapted so that an electromagnetic radiation beam propagating through the fluidic conduit is totally reflected at the reflection layer. Providing such a reflection layer, for instance made from fluoropolymers (Teflon® AF) at an inner surface of the semiconductor oxide tubing may allow to further increase the efficiency of the usage of the electromagnetic radiation beams.

Additionally or alternatively, it is also possible that an outer surface of the semiconductor oxide tubing is lined with a reflection layer adapted so that an electromagnetic radiation beam propagating through the fluidic conduit is totally reflected at the reflection layer. Hence, also an outer surface may be lined, which may be made possible by correspondingly adjusting the refraction indices of the material of the semiconductor oxide tubing and the reflection layer to fulfill the condition that total reflection is only possible at a boundary from a medium with a higher refractive index to a medium with a lower refractive index.

The flow cell may comprise an electromagnetic radiation source adapted for generating an electromagnetic radiation beam and for coupling the electromagnetic radiation beam into the fluidic conduit. Such an electromagnetic radiation source may be a light emitting diode, a laser, a light bulb, or any other electromagnetic radiation source having an appropriate emission wavelength or emission wavelength range. Such an electromagnetic radiation may be coupled into the fluidic conduit delimited by the semiconductor oxide tubing.

The electromagnetic radiation source may be adapted for generating an optical light beam (for instance having a wavelength between about 400 nm and about 800 nm) or an ultraviolet (UV) beam (having shorter wavelengths). The miniature dimensions of the flow cell according to an exemplary embodiment may be appropriate not only for optical applications but also for UV applications, generally for UV-Vis applications.

The flow cell may comprise an electromagnetic radiation detector adapted for detecting the electromagnetic radiation beam after propagation through the fluidic conduit. Such an electromagnetic radiation detector may be arranged to detect light after traveling through the fluidic conduit. Such an electromagnetic radiation detector, for instance a light detector, may comprise a photodiode, a photodiode array or the like capable of generating an electric signal indicative of the corresponding optical signal. It is possible that such an electromagnetic radiation detector comprises a linear or two-dimensional array of photosensitive elements. Such an electromagnetic radiation detector may further comprise additional optical elements such as a grating or the like.

The electromagnetic radiation detector may comprise an optical light detector and/or an ultraviolet radiation detector. The range of sensitivity regarding wavelength of the electromagnetic radiation detector may therefore be adapted to the wavelength of the light used for exciting the system. For instance, the detector may measure electromagnetic radiation absorption by the fluidic sample, electromagnetic radiation reflection by the fluidic sample, electromagnetic radiation fluorescence of the fluidic sample, etc.

The flow cell may comprise a first window element being transparent for electromagnetic radiation and being located at a first end portion of the fluidic conduit, and may comprise a second window element being transparent for electromagnetic radiation and being located at a second end portion of the fluidic conduit opposing the first end portion. Such window elements may define the portions at which the electromagnetic radiation beam is coupled in and is coupled out of the system. Such window elements may be optically transparent end plates having a planar surface which is oriented perpendicular to a direction of the fluid flow.

The electromagnetic radiation source may be adapted for coupling the electromagnetic radiation beam into the fluidic conduit via the first window element. Thus, the beam generated by the electromagnetic radiation source may propagate through the first window element, from there via total internal reflection through the fluidic conduit defined by the semiconductor oxide tubing, and may leave the optical path via the second window element, to be subsequently directed onto the detector.

The flow cell may further comprise a first optical coupler element arranged between the electromagnetic radiation source and the fluidic conduit to couple the electromagnetic radiation from the electromagnetic radiation source into the fluidic conduit. Such a first optical coupler element may be an optical fiber which may be inserted in a manner so as to sandwich the first window with the semiconductor oxide tubing, and a second optical coupler element may be arranged between the semiconductor oxide tubing on the one hand and the detector on the other hand to provide for a symmetric configuration. Via such optical fiber pieces (such as a light fiber) or any other waveguides, it is possible to precisely control the optical path to thereby achieve an optimum of light efficiency, or in other words to keep the light loss as small as possible.

The flow cell may further comprise a fluid supply hole formed in the semiconductor oxide tubing for supplying the fluidic sample from a connected fluidic component to the fluidic conduit. Such a fluid supply hole may be formed as a bore in the semiconductor substrate and may have an orientation essentially perpendicular to a fluid flow direction of the fluidic conduit. Via the fluid supply hole, a fluidic sample, for instance originating from an outlet of a separation column such as a chromatographic column, may be injected into the fluidic conduit for detection purposes. Thus, the fluid supply hole may be adapted for a fluidic connection to a processing element, particularly a separation column. A sealing of the fluid traveling via the fluid supply hole through the fluidic conduit may be realized by a press seal configuration, such as a hole-to-hole connection between the fluid supply hole in the flow cell and the column. The fluid supply hole may be formed in the semiconductor substrate for supplying the fluidic sample to the fluidic conduit.

The flow cell may further comprise a fluid drain hole formed in the semiconductor oxide tubing for draining the fluidic sample from the fluidic conduit. The fluid drain hole may be arranged symmetrically to the fluid supply hole and may be formed with a similar technology in another end portion of the semiconductor oxide tubing. It may also be formed in the semiconductor substrate for draining the fluidic sample from the fluidic conduit and may guide the separated and detected fluidic sample to a fractioner, a waste container or the like.

The flow cell may comprise a plurality of independently operable fluidic conduits each delimited by a semiconductor oxide tubing connected to a common semiconductor substrate. Thus, multiple optical and fluid flow paths may be formed in a shared semiconductor substrate for separate (for instance parallel) operation. This may allow to parallelize fluid analysis operations such as fluid separation analysis, to provide for high throughput applications.

M. Najmzadeh, S. Haasl, P. Enoksson, "A Straight Silicon Tube as a Microfluidic Density Sensor", Proceedings of the 11th international conference on miniaturized systems for chemistry and life sciences pp. 536-538, No. 47833 discloses a density sensor based on a silicon straight tube. Corresponding manufacturing methods may be implemented according to exemplary embodiments for manufacturing flow cells.

In the following, further exemplary embodiments of the fluidic device will be explained. However, these embodiments also apply to the detector device and the method.

The fluidic device may comprise a processing element filled with a separating material. Such a separating material which may also be denoted as a stationary phase may be any material which allows an adjustable degree of interaction with a sample so as to be capable of separating different components of such a sample. The processing element may be arranged in a fluidic path upstream the detector so that fractions of a sample separated by the processing element may be subsequently detected by the detector device.

The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 μm to essentially 50 μm. Thus, these beads may be small particles which may be filled inside the separation section of the microfluidic device. The beads may have pores having a size in the range of essentially 0.01 μm to essentially 0.2 μm. The fluidic sample may be passed through the pores, wherein an interaction may occur between the fluidic sample and the pores.

The fluidic device may be adapted as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be adapted as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the column. Due to the different interaction of the different protein fractions with the filling of the column (for instance using a liquid chromatography device), the different samples may be distinguished, and one sample or band of material may be selectively isolated as a purified sample.

The fluidic device may be adapted to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and analyzed.

The processing element may be a chromatographic column for separating components of the fluidic sample. Therefore, exemplary embodiments may be particularly implemented in the context of a liquid chromatography apparatus.

The fluidic device may be adapted to conduct the mobile phase through the system with a high pressure, for instance of 50 bar to 100 bar, particularly of at least 600 bar, more particularly of at least 1200 bar.

The fluidic device may be adapted as a microfluidic device. The term "microfluidic device" may particularly denote a fluidic device as described herein which allows to convey fluid through microchannels having a dimension in the order of magnitude of less than 500 μm, particularly less than 200 μm, more particularly less than 100 μm or less than 50 μm or less.

In the following, further exemplary embodiments of the method will be explained. However, these embodiments also apply to the flow cell and to the fluidic device.

The method may comprise forming the semiconductor oxide tubing by converting a part of the semiconductor substrate from semiconductor material into semiconductor oxide material, for instance by a chemical reaction. In this context, the term "converting" may denote that material which originally forms part of the semiconductor substrate is treated in such a manner as to subsequently form part of the material which represents the semiconductor oxide material. This may be performed by thermally oxidizing a surface portion of the semiconductor substrate, for instance by exposing this material to a high temperature and oxygen atmosphere, thereby converting silicon material into silicon oxide material.

The method may further comprise forming the semiconductor oxide tubing by thermally annealing a surface of the semiconductor substrate. After having thermally oxidized a surface of the semiconductor substrate, it may be advantageous or appropriate to reduce mechanical stress in such a material by performing a thermal annealing procedure. This may again include heating the material in a specific atmosphere. A flow cell according to an exemplary embodiment may be a quartz capillary which can be a small structure susceptible to breakage which, during operation, may be subject to high mechanical stress. It may be advantageous to take measures for reducing stress, for instance to provide for a stress relief structure or a flexible structure. For instance, the expansion coefficient of silicon may differ significantly from the expansion coefficient of silicon oxide. Hence, during conversion of silicon to silicon oxide or later during operation of the flow cell, mechanical stress may act on the converted material. Providing a mechanically flexible component in the member may allow the member to balance out such mechanical stress, thereby allowing a user to employ the member even under harsh conditions.

The method may further comprise forming the semiconductor oxide tubing by depositing semiconductor oxide material on a surface of the semiconductor substrate. In such a scenario, the semiconductor substrate may form the template or basis for the subsequent deposition of semiconductor oxide material which, due to the chemical similarity of semiconductor oxide (such as silicon oxide) and corresponding semiconductor material (such as silicon) will not generate significant mechanical stress in a boundary portion, particularly since the lattice configurations of the semiconductor and its semiconductor oxide are usually not too different from one another, particularly in the case of the material pair silicon and silicon oxide.

The method may further comprise patterning the semiconductor substrate before forming the semiconductor oxide tubing. By such a patterning, a recess may be formed in the semiconductor substrate defining the geometry of the fluidic conduit. By thermally oxidizing a surface and/or by depositing a semiconductor oxide material subsequently onto this recess, it is possible to properly define the geometry of the fluidic conduit simply by adjusting the patterning procedure. Such a patterning may include the application of lithography, particularly illumination and etching procedures.

The method may comprise patterning the semiconductor substrate by anisotropic etching of material of the semiconductor substrate before forming the semiconductor oxide tubing. Such an anisotropic etching (with etching rates being different in the different spatial directions) may make use of an anisotropy of a crystalline substrate regarding etching into different directions. For instance, when a crystalline silicon substrate is etched along a <100> crystal lattice plane, a symmetric trapezoidal recess may be formed which can form the basis of a half hexagonal lumen.

The method may further comprise patterning the semiconductor substrate by mechanically weakening a selective surface portion of the semiconductor substrate and subsequently removing the mechanically weakened surface portion. For this purpose, DRIE (Deep Reactive Ion Etching) may be employed.

Such a mechanical weakening may particularly be performed by forming a comb-shaped semiconductor structure (by lithography and etching) in a surface portion and by subsequently oxidizing the individual fingers of the comb-shaped structure. Oxidizing a surface portion of a silicon substrate by heat and an appropriate chemical environment will usually affect only a surface portion of the silicon material. When a comb structure with very small comb elements or fingers is formed having a thickness so that the entire finger or comb element structure is prone to conversion of silicon material to silicon oxide material by thermal oxidizing, this may allow to manufacture a side wall of the later flow cell.

Particularly, the method may comprise patterning the semiconductor substrate by anisotropically etching along a <100> plane before forming the semiconductor oxide tubing to thereby form a trapezoidal recess in the semiconductor substrate. This is a tricky way of defining the surface geometry of the semiconductor substrate for a subsequent formation of the semiconductor oxide tubing. Particularly, the semiconductor substrate may be patterned by the anisotropic etching along the <100> plane so that slanted side walls of the trapezoidal recess correspond to a <111> plane of the semiconductor substrate.

The semiconductor oxide tubing may be formed in a recess of the semiconductor substrate formed by patterning the semiconductor substrate. Then, two semiconductor substrates both being processed in the described manner, i.e. both having a section of a semiconductor oxide tubing in a recess, may be bonded in such a manner that the recesses together form the fluidic conduit. By such a procedure, a for instance hexagonal lumen may be enclosed by the semiconductor substrates being bonded to one another.

The method may further comprise selectively removing a part of the material of at least one of the two semiconductor substrates. By taking this measure, it is possible to expose the semiconductor oxide tubing by using a boundary between semiconductor and semiconductor oxide as a stopping layer for a corresponding etching procedure. Selectively removing the part of the material of the at least two semiconductor substrates may be performed by etching, particularly by wet etching. However, such an etching procedure may also be performed in a chemically aggressive gas or plasma atmosphere.

The method may comprise lining a surface, particularly an inner surface, of the semiconductor oxide tubing with a reflection layer adapted so that an electromagnetic radiation beam propagating through the fluidic conduit is totally reflected at the reflection layer. Such a lining may include properly selecting the refraction indices of the two adjacent materials so that, in accordance with physical laws, total internal reflection becomes possible.

Particularly, the lining may comprise conducting a lining material through the fluidic conduit (for instance in a liquid phase state) and subsequently solidifying, particularly by sintering, the conducted lining material at an inner wall of the fluidic conduit to thereby form the reflection layer. This is a simple procedure allowing to properly define the material, the thickness and other parameters of the inner lining.

The method may comprise forming a cover structure covering an outer surface of the semiconductor oxide tubing, the cover structure having a refraction index being smaller than a refraction index of the fluidic surrounding (for instance a mobile phase, a sample to be analyzed, etc.). By such a cover structure with the described material properties it is possible to ensure that internal reflection of light beams propagating through the fluidic conduit and/or through the semiconductor oxide tubing may take place at a boundary between the semiconductor oxide tubing and the cover structure.

In an embodiment, the semiconductor oxide may be formed based on the semiconductor. In other words, the semiconductor oxide may correspond to the corresponding semiconductor material. The semiconductor oxide may be particularly formed on the basis of the semiconductor, by a corresponding material conversion.

Traditional UV cells are fabricated by traditional machining methods, and are thus limited in their minimum load size. Also, the traditional machining methods do not lend themselves well to parallel cells of close pitch (1 mm or below).

Exemplary embodiments make use of micromachining methods to create a total internal reflection cell, with parallel cells allowed on the same chip. The micromachining techniques may allow for a low cell volume, and a tight pitch. Such a cell may also be free of reflecting metal thin films that might degrade over time.

In the push for smaller cell size and parallelism in UV detection systems, exemplary embodiments may employ fabrication techniques that allow for small cell volumes and a tight pitch. Also, being a total internal reflection cell, light may be guided in the cell with dielectrics, without the use of metal thin films. This may be generally believed to give a longer lasting UV cell.

In an embodiment, micromachining techniques may be used to build miniature UV detection cells, wherein a plurality of cells can be fabricated from a single substrate. There may be a number of ways to fabricate such a cell.

More generally, exemplary embodiments may provide a free standing capillary that is clamped along a mechanically robust frame. There in fact can be a plurality of capillaries that have a fluid input along the mechanically robust frame, a free standing region where detection can occur in the capillary, and a fluidic exit along the frame. Light can be coupled into the cell by another opening in the frame. It is also possible to provide for a secondary fluid, other than air, and with specific dielectric properties, to surround the capillaries. This can be realized by bonding additional wafers to the structure.

In an embodiment, it may be advantageous to surround the quartz capillary with air, to allow for a total reflexion of light within the capillary. However, surrounding air under atmospheric pressure will not contribute significantly to the mechanical stabilization of the sensitive quartz capillary. Hence, it may be possible to mechanically protect the quartz capillary against mechanical damage, for instance in response to the application of high pressure of, for instance, 100 bar. For this purpose, it may be possible to embed the quartz capillary in a material having a smaller refraction index than quartz. Such a surrounding medium may be a solid, a liquid or even a gas. When using a gas (such as air or nitrogen or a noble gas like Xenon), it is possible to provide the gas under pressure, for instance at a pressure of 200 bar. By applying mechanical pressure using a surrounding gas (which may be accommodated with high pressure in a chamber surrounding the quartz capillary) it is possible to mechanically protect the device so that the device may be used over a broad operation range.

In an embodiment, a pressure relief valve may be provided which can be used in a failure event causing the pressure to rise above an allowed maximum value that the capillaries can withstand.

A fluid may be guided through a channel formed by semiconductor processing technology. A polychromatic light source may emit a polychromatic light beam propagating through the fluidic conduit so as to interact with different fractions in the fluidic sample propagating through the channel. A spectrometer with a grating and a photodiode array (for instance a linear line of photodiodes) may then detect the resulting secondary light beam. Exemplary embodiments may provide for a liquid waveguide flow cell, particularly for liquid chromatography applications such as micro liquid chromatography applications (<100 µl/min.) or even nano liquid chromatography applications (<1 µl/min., for instance 10 nl/min. to 500 nl/min.).

According to an exemplary embodiment, a total analysis system in microtechnology may be provided. Thus, not only a flow cell may be formed in a silicon wafer or a glass wafer, but it is also possible to manufacture an integrated separation column. An example for such an integrated column may be a pillar column. It is also possible to combine the monolithically integrated flow cell with a HPLC chip which can be made of polyimide material. Alternatively, such a flow cell may also be used as a stand-alone flow cell.

For high throughput applications, it is possible to parallelize flow cell detection in, for instance, 8 or 10 flow cells monolithically integrated in a single wafer.

The light conductance value of a flow cell may dramatically decrease with increasing length of the cell. However, a smaller light conductance value may also result in a smaller photon flow and hence a smaller signal-to-noise ratio. In an optical system, the smallest light conduction value defines the entire conduction value. Larger path lengths may be realized with a total internal reflection (TIR) based flow cell. Exemplary embodiments may also provide for UV flow cells for the nano flow region where such an UV flow cell might substitute conventionally used mass spectrometer detectors.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
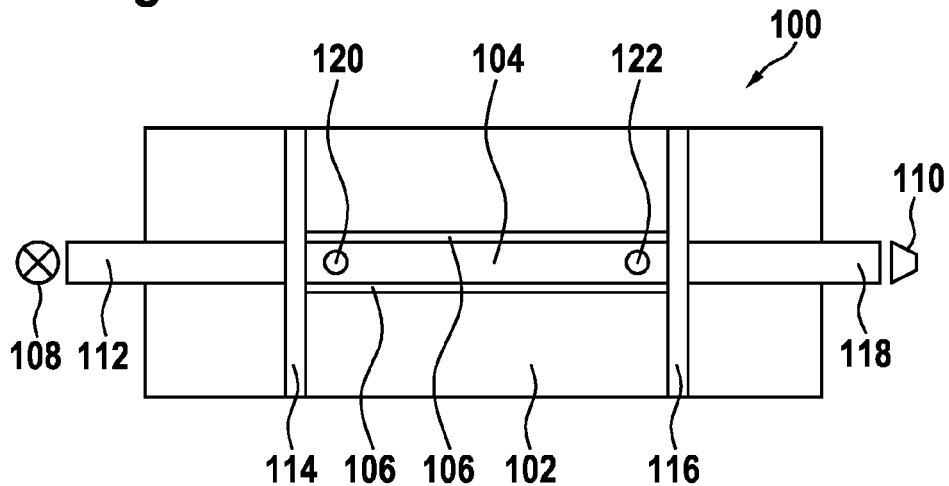
FIG. 1 illustrates a monolithically integrated flow cell according to an exemplary embodiment.

The illustration in the drawing is schematically.

FIG. 1 illustrates a monolithically integrated flow cell 100 according to an exemplary embodiment.

FIG. 1 illustrates a cross-sectional view in a plane parallel to a surface plane of a crystalline silicon substrate 102. Within the silicon substrate 102, a fluidic conduit 104 is formed which is delimited by an optically transparent silicon oxide tubing 106 which is, in turn, monolithically formed with or from the silicon substrate 102. As can be taken from FIG. 1, the silicon oxide tubing 106 is embedded in the semiconductor substrate 102.

The flow cell 100 further comprises for instance a light emitting diode 108 as an electromagnetic radiation source for generating a light beam and for coupling the light beam into a lumen formed by the fluidic conduit 104. The flow cell 100 further comprises an electromagnetic radiation detector 110, for instance an optic spectrometer, comprising a linear photodiode array and a grating. An electromagnetic radiation beam generated by the light source 108 may be inserted into a first optical coupler element 112 such as optical fiber or an integrated waveguide, may propagate through an optically transparent first end plate 114, may propagate through the conduit 104 while being totally reflected at the silicon oxide tubing 106, will propagate through a second contact window 116 also made of optically transparent silicon oxide material, will then propagate through a second optical coupler element 118 in the form of a second optical fiber or an integrated waveguide and will from there be directed into and detected by the optical detector 110.

A first fluid supply hole 120 (extending perpendicularly to the paper plane of FIG. 1) is formed to be in fluid communication with the semiconductor oxide tubing 106 for supplying a fluidic sample to the fluidic conduit 104. Although not shown in FIG. 1, the fluid supply hole 120 is in fluid connection with an outlet of a chromatographic column for separating different fractions of a fluid. These different fractions may then be detected optically in the flow cell 100.

A drain hole 122 (extending perpendicularly to the paper plane of FIG. 1) is formed to be in fluid communication with the semiconductor oxide tubing 106 as well for draining the fluidic sample from the fluidic conduit 104 after having traversed the optical and fluidic path between the fluid supply hole 120 and the fluid drain hole 122.

In the following, referring to FIG. 2 to FIG. 7, a method of manufacturing a flow cell 100 according to an exemplary embodiment will be explained.

Figure 2:
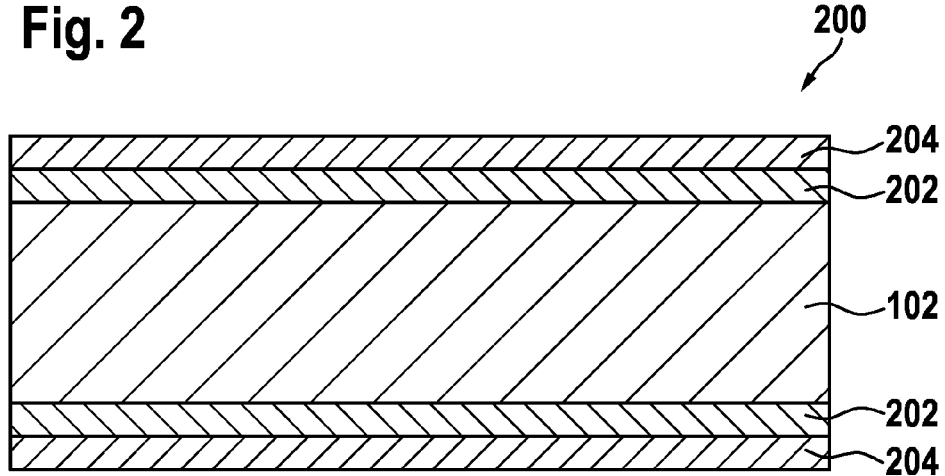
FIG. 2 to FIG. 7 show layer sequences obtained during a method of manufacturing a monolithically integrated flow cell according to an exemplary embodiment.
Figure 3:
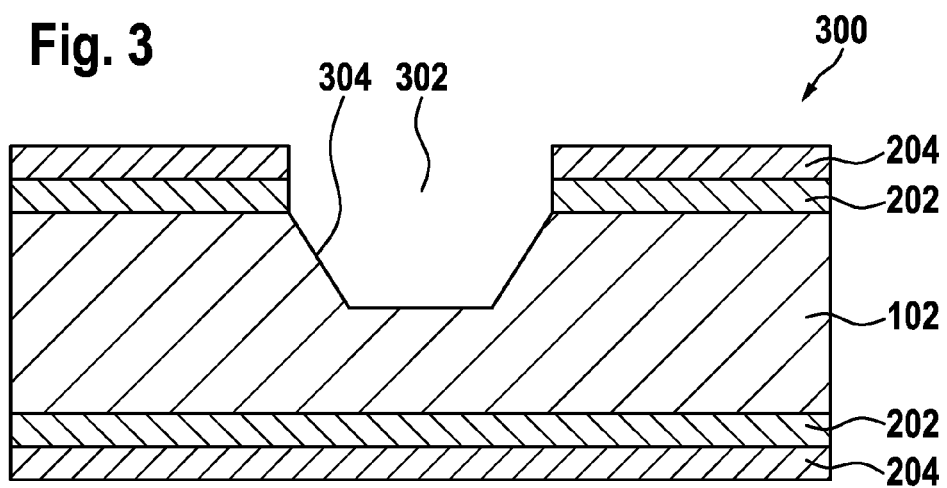

FIG. 2 shows a layer sequence 200 obtained by first depositing a silicon oxide layer 202 on opposing exposed surface portions of a silicon substrate 102. Then, an optional silicon nitride layer 204 may be deposited on top of the silicon oxide layers 202.

Subsequently, a surface portion of one of the two opposing main surfaces of the silicon substrate 102 is exposed by patterning the double insulating layer 202, 204 by etching to form an access hole 302. The result is a layer sequence 300 shown in FIG. 3. After having formed such an access hole 302, the resulting layer sequence may be made subject of a wet etch procedure, for instance using Potassium Hydroxide (KOH) solution for crystallographic etching of Silicon. The consequence is that, since the etching of the <100> wafer 102 is an anisotropic etching procedure, a trapezoidal recess 304 is formed.

Figure 4:
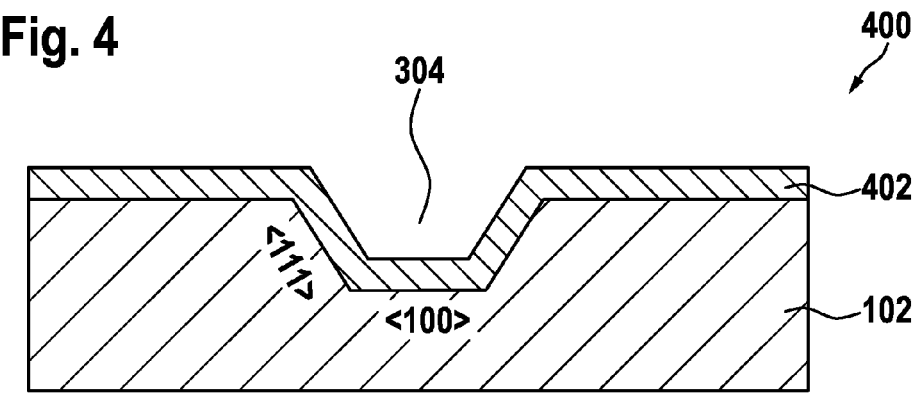

FIG. 4 shows in more detail a <100> plane and a <111> plane of the silicon substrate 102. In order to obtain a layer sequence 400 shown in FIG. 4, the silicon oxide layer 202 and the silicon nitride layer 204 are removed by etching procedures. By thermally oxidizing a surface of the patterned silicon substrate 102, a further silicon oxide layer 402 may be formed which is optically transparent. The procedure shown in FIG. 4 can be repeated with a second wafer in a simultaneous way.

Figure 5:
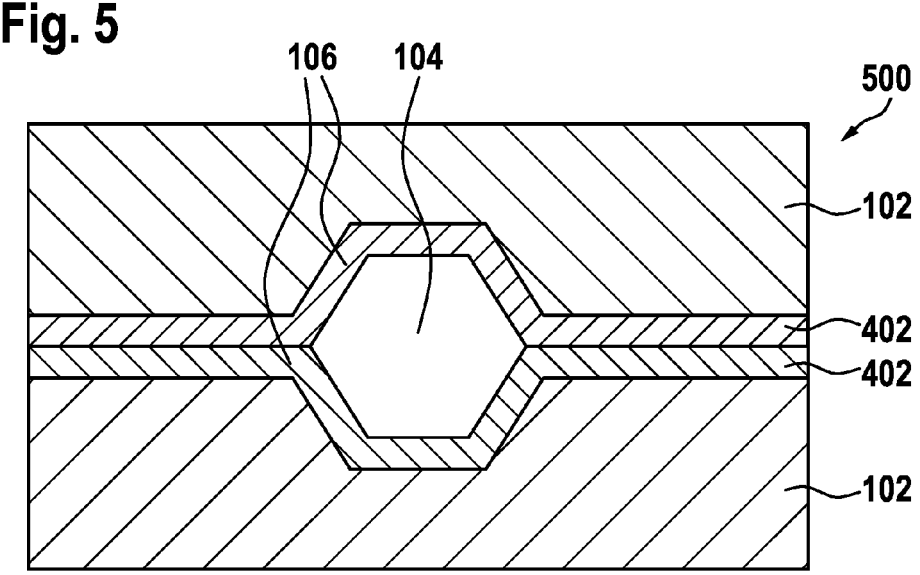
Figure 6:
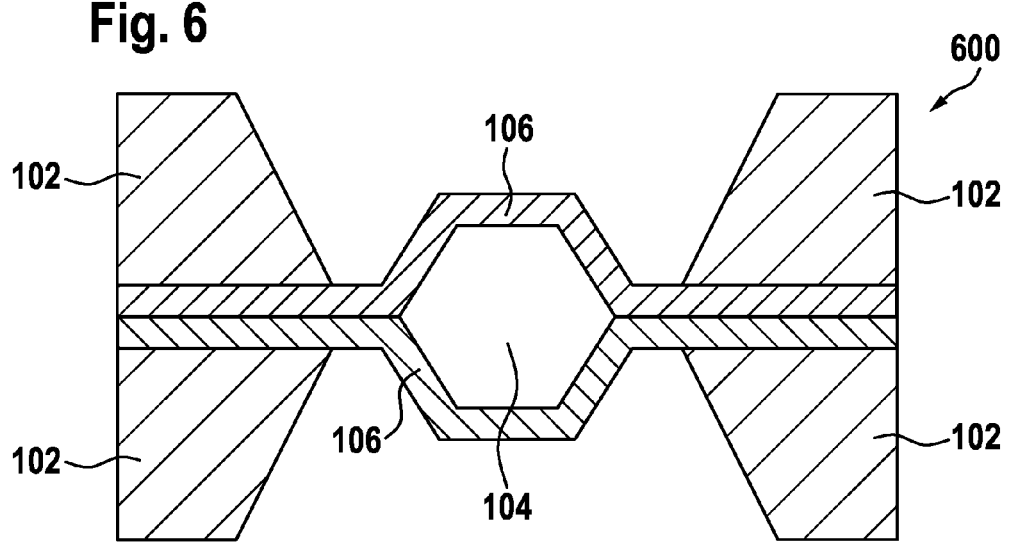

Two wafers processed in such a manner may then be connected to one another by bonding, and a result of this is shown as a layer sequence 500 in FIG. 5. By bonding the two wafers 400 in a way that the recesses 304 are aligned to one another, a fluidic conduit 104 is formed which is delimited along an entire circumference thereof by the silicon oxide tubing 106 formed by the two bonded further silicon oxide layers 402.

By patterning (as before) and a treatment with an appropriate chemical, for instance KOH, portions of the semiconductor substrate 102 may be removed, thereby exposing the fluidic conduit 106. The result is shown as a layer sequence 600 in FIG. 6.

Figure 7:
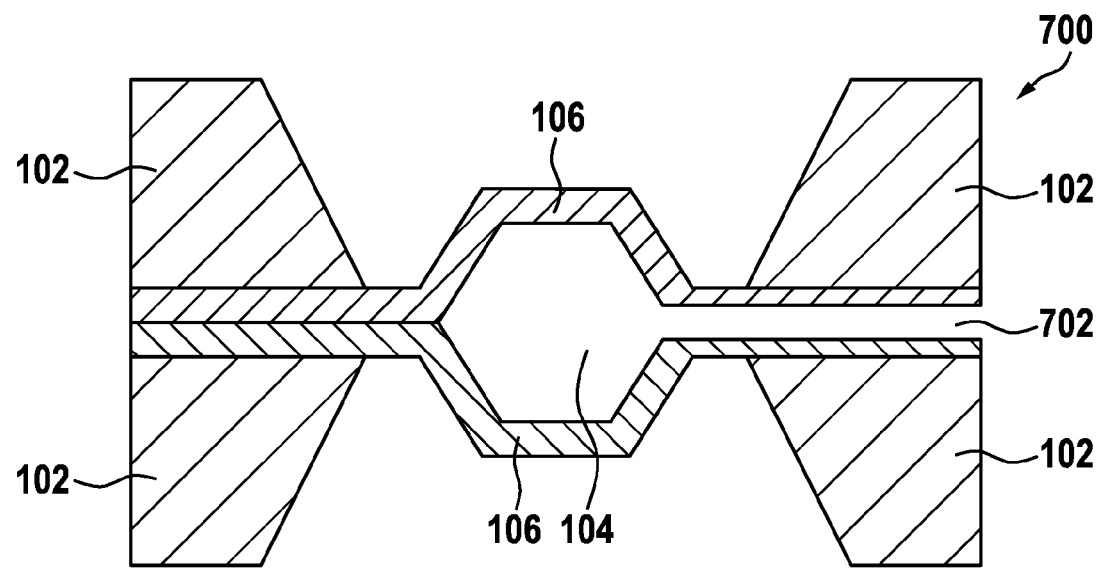

Optionally, a lateral section of the silicon oxide structure 106 may be removed to thereby form a fluid supply or fluid drain hole 702, as shown in a layer sequence 700 in FIG. 7.

Figure 8:
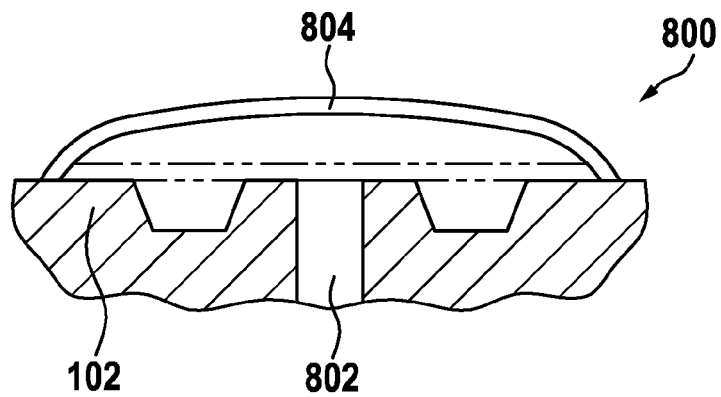
FIG. 8 illustrates a pressure relief valve which can be implemented in a monolithically integrated flow cell according to an exemplary embodiment.

The layer sequence 700 is suitable for high pressure applications of 100 bar or more. However, it may be appropriate to provide a pressure relief valve, as the one shown in FIG. 8 and denoted with reference numeral 800 in order to seal the 10 various conduits also in the presence of high pressure. For example, in the substrate 102, a fluidic channel 802 may be formed which is open in the scenario shown in FIG. 8. A flexible membrane 804 may be formed over the fluidic conduit 802. By applying a pressure on the membrane 804, the valve 800 may open , as indicated with solid lines in FIG. 8.

Figure 9:
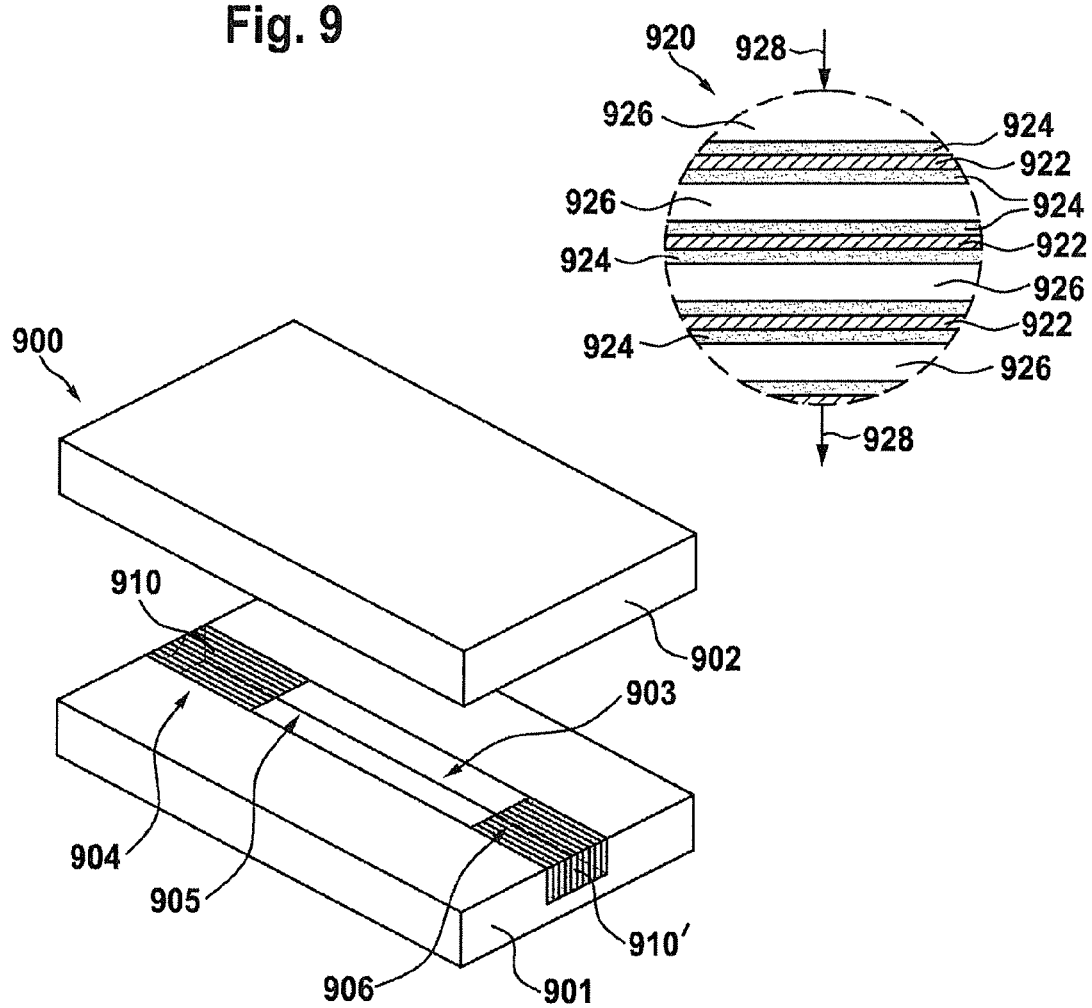
FIG. 9 illustrates a HPLC chip with a pillar configuration which can be implemented in a monolithically integrated flow cell according to an exemplary embodiment.

The flow cells 700 or 100 may be used in combination with a chip-like fluidic device with a chip-like separation column as shown in FIG. 9. It is also possible to monolithically integrate such a separation column together with the flow cell 100 or 700 in a common substrate.

The microfluidic device 900 shown in FIG. 9 comprises a first essentially planar member 901 and a second essentially planar member 902. In an operation state in which the first essentially planar member 901 is coupled to the second essentially planar member 902 (for instance using a gluing connection to form a laminated structure), a column tube is formed in a recess 903 which is formed in the first essentially planar member 901 and using the planar surface of the second essentially planar member 902 as a lid. The recess 903 forms, when the members 901 and 902 are connected to one another, a channel-like structure which has a similar function as a conventional liquid chromatography separation column.

The microfluidic device 900 can be configured and used in a similar manner as described in FIGS. 6A and 6B and corresponding description of US 2004/0156753 A1.

The flat surface 902 can be formed by any solvent resistant material, including, but not limited to, polymer or glass. The patterned polymer substrate 901 can be formed using any fabrication technique, including embossing, laser ablation, injection molding, etc. It should further be understood that the microfluidic device 5 200 can include multiple channels 903, and each channel 903 can include a microstructured body 920 having a surface covered with porous material 924 which can be inserted as a single piece in the channel 903, more precisely in a central portion 905 thereof.

Optional frits 910,910' are arranged in end portions 904, 906 of the recess 903 10 to further increase stability, but can alternatively be omitted. As shown in FIG. 9, the channel 903 is divided into three portions, namely a first portion 904 filled with a first frit 910, a second central portion 905 filled with a microstructured body 920, and a third portion 906 filled with the second frit 910'.

An enlarged view of a solid fluid separation member 920 to be inserted in the channel 903 shows the microstructured body 922 in the form of parallel aligned pillars, wherein a layer of porous material 924 covers the pillars 922. Between the pillars 922 covered with the porous layer 924, fluidic paths 926 are formed which may also be denoted as channels. The pillars 922 are arranged in parallel to one another and have a diameter of 3 µm. The channels 926 have a diameter of 4 µm. The porous material 924 has a thickness of 0.5 µm. The microstructured body 922 defines a spatially regular pattern of the channels 926. The porous material 924 has a uniform thickness over the entire surface of the microstructured body 922. The pillars 922 are cylindrically shaped. Although not shown in FIG. 9, the pillars 922 are arranged in a matrix-like pattern. The body on the basis of which the microstructured pillars 922 have been manufactured is a three-dimensional substrate. Thus, all pillars 922 are connected to one another to form one single integrally formed body. The pillars 922 may be made of silicon material and the porous layer 924 may be made of permeable silicon oxide material.

As an alternative to the pillar arrangement 920, it is also possible to insert fluid separation beads into the fluidic channel 905.

More generally, a flow cell according to an exemplary embodiment may be combined with a pillar column in a common semiconductor substrate. For instance, flow cell and pillar column may be processed based on a shared silicon wafer. Thus, both components may be manufactured in a shared microprocessing environment.

In another embodiment, flow cell and pillar column may be processed separately and may then be combined to form a hybrid-type analysis device. In one embodiment, the pillar column may be directly connected to the flow cell. In another embodiment, the pillar column may be coupled to the flow cell via an adapter such as an intermediate plate or layer. Such a layer may be for instance sprayed on one of the components or may be a separate layer sandwiched between the flow cell and the pillar column.

In still another embodiment, a planar column chip (such as the polymer chip 900 for instance comprising beads or a pillar structure) may be connected to a flow cell according to an exemplary embodiment. Such components may be connected directly to one another without an adapter piece in between. Such a direct connection can be realized by a pressure seal or a bore-to-bore connection or a plug connection. When the column chip is made of a soft material such as a polymer material, the soft or flexible material may provide for an efficient sealing in a leakage-free way. A planar geometry of a column chip may fit properly with a geometry of a flow cell. However, in another embodiment, an adapter piece may be arranged between column chip and flow cell, for instance as described above.

In the following, referring to FIG. 10 to FIG. 24, another method of manufacturing a flow cell according to another exemplary embodiment will be explained.

Figure 10:
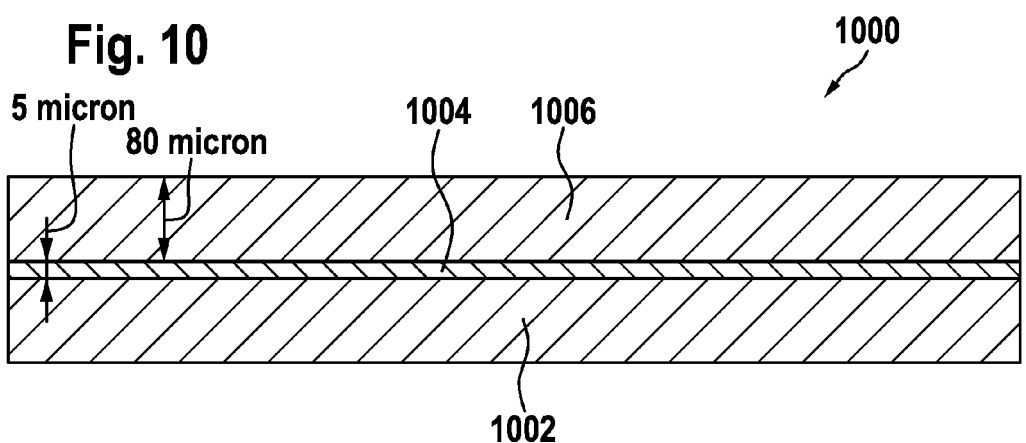
FIG. 10 to FIG. 24 show layer sequences obtained during a method of manufacturing a monolithically integrated flow cell according to another exemplary embodiment.

Starting point is a layer sequence 1000 shown in FIG. 10. A buried silicon oxide layer 1004 is embedded between a bulk silicon substrate 1002 and an active wafer silicon layer 1006. The active wafer layer 1006 will define the height of the flow cell to be manufactured, that is the cell height will be about twice that of the thickness of the active wafer 1006. In the given example, the active thickness is shown to be 80 µm. The buried oxide layer may be, for instance, 5 µm. The width may be determined by the layout.

Figure 11:
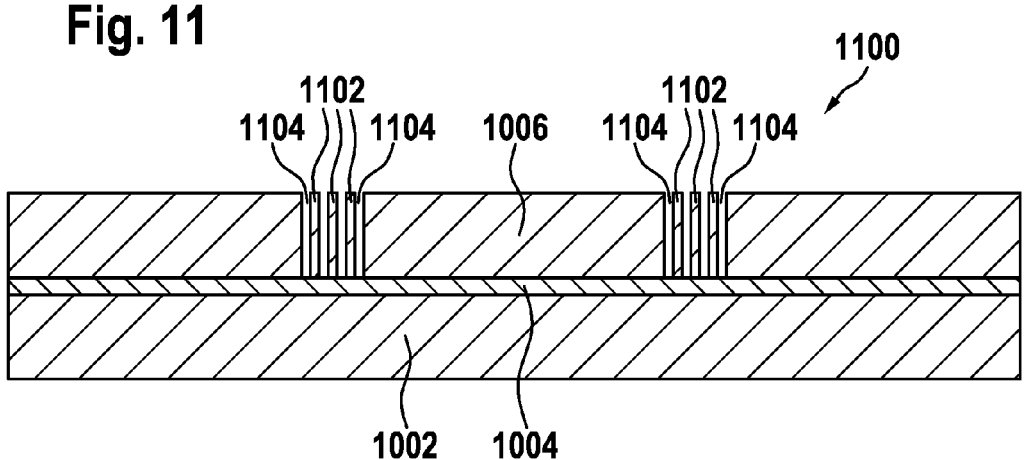

On the basis of the SOI silicon substrate 1000, a comb structure 1102 may be formed by a corresponding patterning and etching procedure, as shown in a layer sequence 1100 illustrated in FIG. 11. Deep reactive ion etching (DRIE) may be used to form trenches 1104 which separate individual comb elements of the comb structure 1102 in the active wafer layer 1006.

Figure 12:
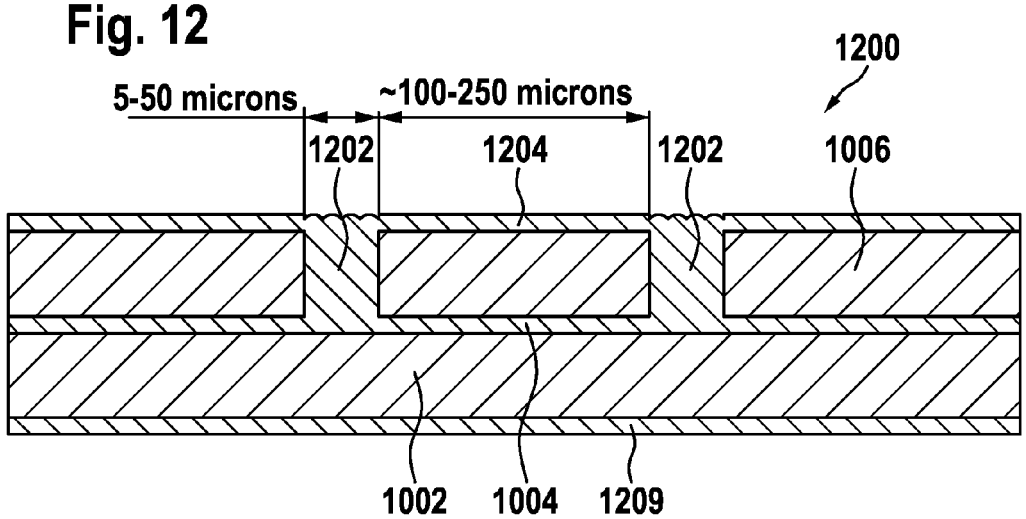

The comb fingers are so thin that subsequent thermal oxidation of the layer sequence 1100 will result in a layer sequence 1200 shown in FIG. 12 which comprises completely oxidized silicon oxide regions substituting the former comb elements. Thus, a silicon oxide block 1202 may be formed in a surface of the active layer 1006 which is also covered by a silicon oxide layer 1204. Thus, an oxidation procedure will lead to a thick oxide on the silicon surfaces which will be thick enough to completely consume the trenched silicon, forming the thick thermal oxide structure 1202. This technique is used to make a thick thermal oxide for semiconductor applications.

Figure 13:
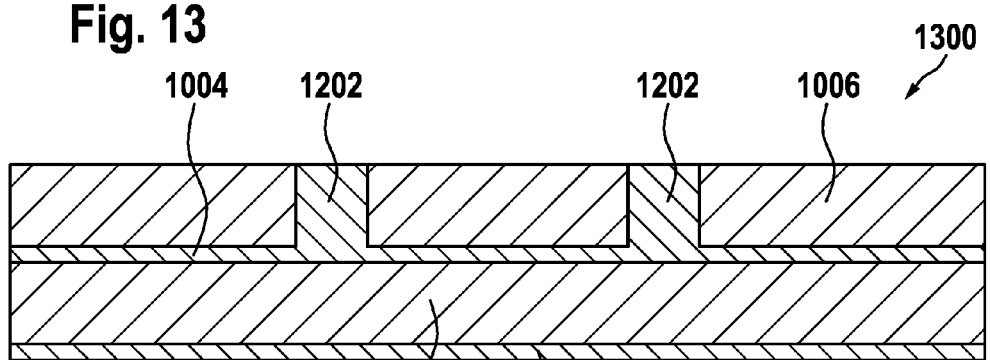

A layer sequence 1300 shown in FIG. 13 may be obtained by performing CMP (chemical mechanical planarization) for removing silicon oxide material using silicon material as a stop material. This may allow to planarize the upper surface and to remove the silicon oxide layer 1204 from an upper surface of the layer sequence 1200.

Figure 14:
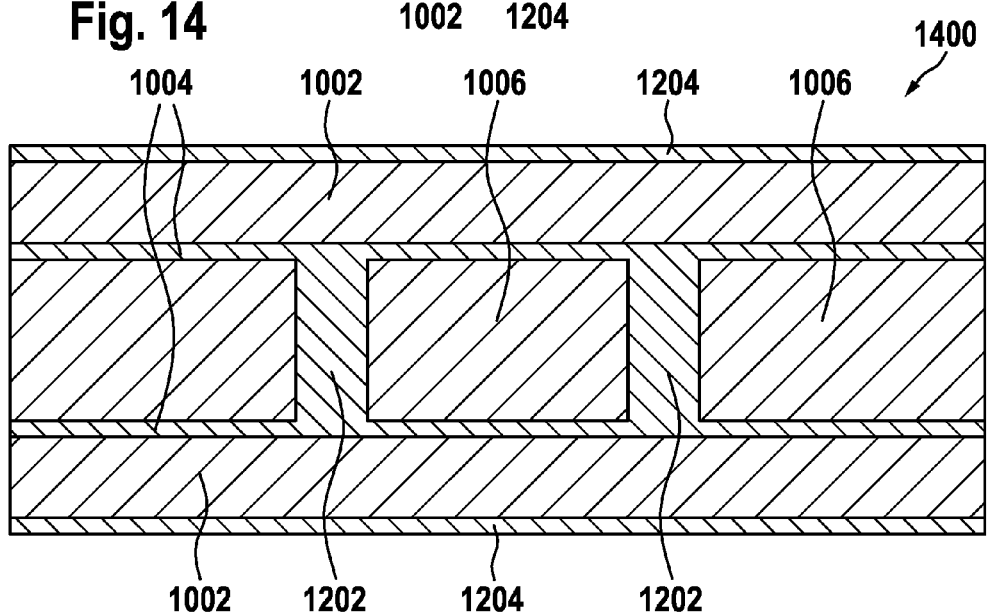

A layer sequence 1400 shown in FIG. 14 may be obtained by a fusion bonding of two wafers of the type shown in FIG. 13. Two wafers 1300 that have gone through identical processing are bonded together, leaving a wafer structure 1400 with buried oxides of varying thickness.

Figure 15:
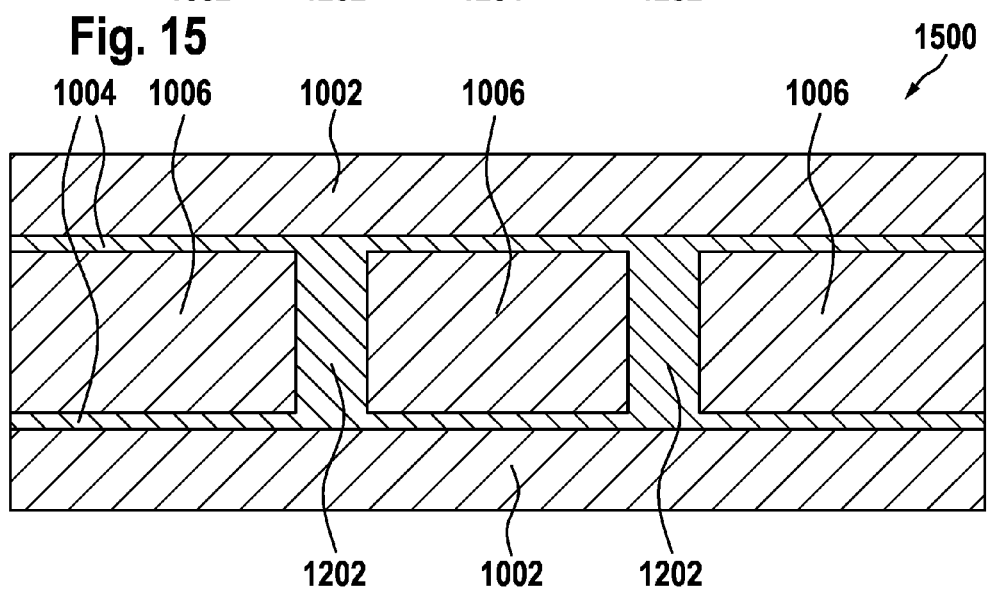

In order to obtain a layer sequence 1500 shown in FIG. 15, the surface oxide layers 1204 are removed from the layer sequence 1400 by stripping. During such a procedure, the silicon oxide layers 1204 on the outer surfaces of the layer sequence 1400 are removed with HF, or any other selective etchant.

Figure 16:
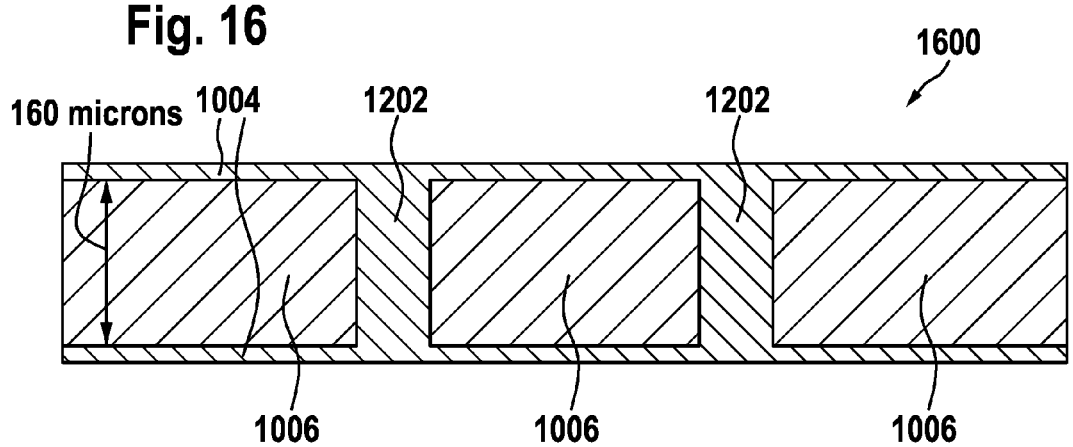

In order to obtain a layer sequence 1600 shown in FIG. 16, a silicon etch (or polish and etch) may be performed using silicon oxide material as stop layers. By taking this measure, the outer silicon material of the layer sequence 1500 is removed, using a selective silicon etchant (for instance a low pH TMAH solution). This outer silicon may remain on some regions on the underside of the wafer to produce added mechanical integrity.

Figure 17:
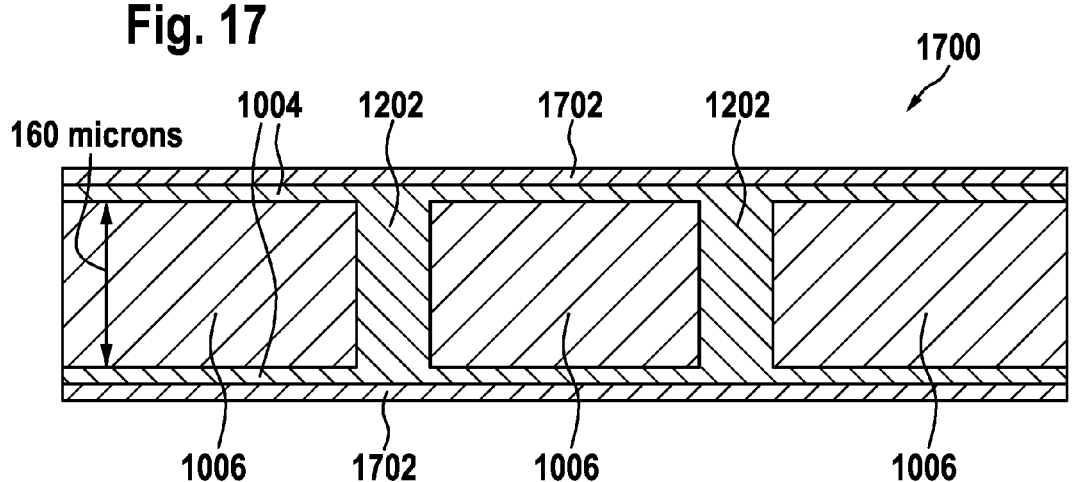

In order to obtain a layer sequence 1700 shown in FIG. 17, a dual sided tube oxide deposition (for instance of 5 microns) may be performed. This may form a deposited silicon oxide layer 1702 which is added to thicken up the pre-existing thermal oxide 1004. This will provide added mechanical strength to the roof and floor of the cell.

Figure 18:
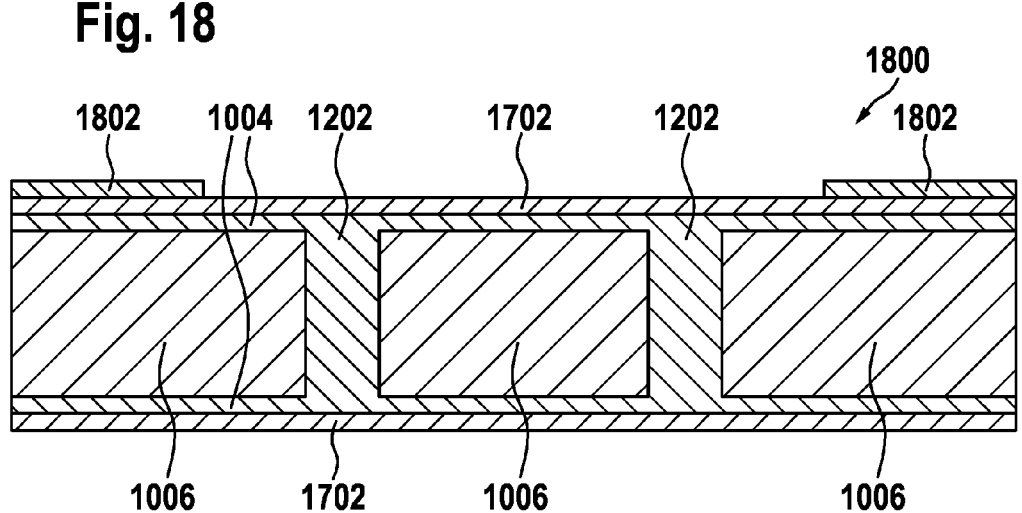

In order to obtain a layer sequence 1800 shown in FIG. 18, a gold (Au) deposition and patterning may be performed (shadow mask or lift off, for instance) to thereby manufacture gold contacts 1802. Thus, the gold material is deposited and patterned selectively, and may be used for a thermo compression bond in a later procedure.

Figure 19:
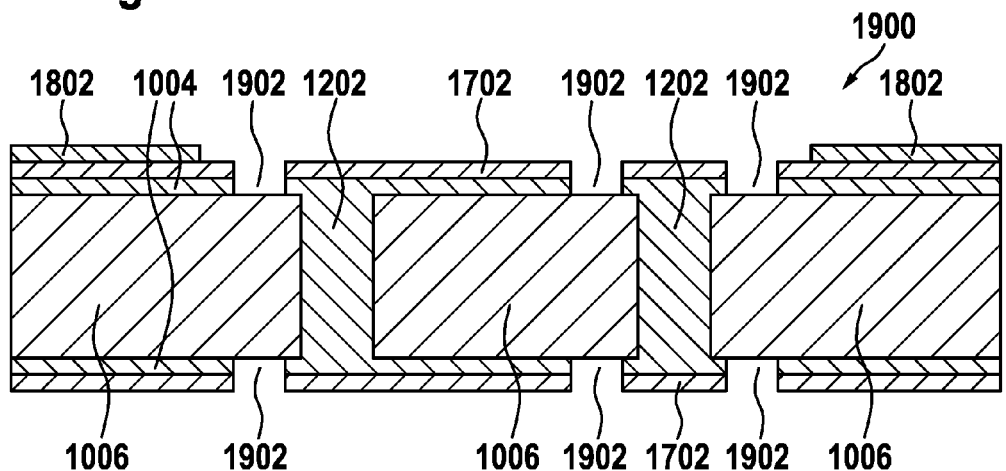

FIG. 19 shows a layer sequence 1900 which may be obtained by a selective silicon oxide removal procedure. Thus, vias 1902 may be cut out in the silicon oxide material to make access for later silicon removal.

Figure 20:
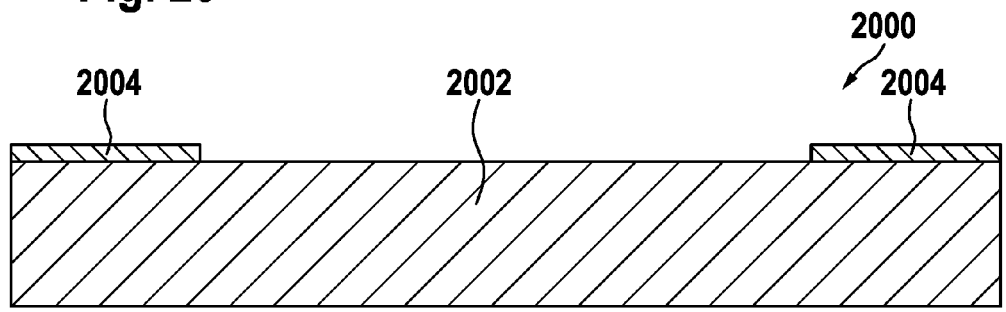

FIG. 20 shows a layer sequence 2000 made of a glass wafer 2002 (need not be UV-transparent) which is also provided with a patterned gold layer 2004.

Figure 21:
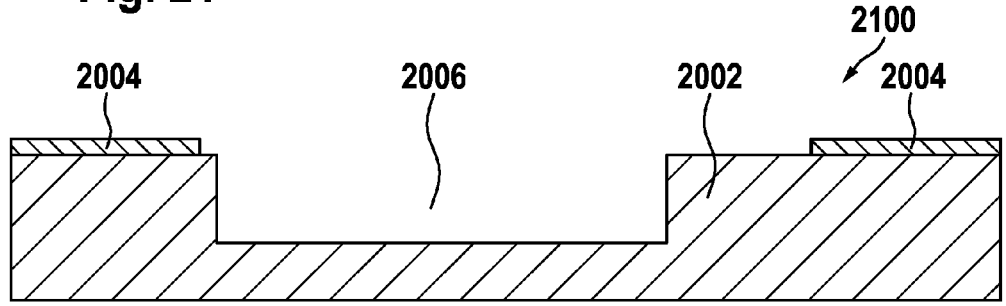

FIG. 21 shows a layer sequence 2100 in which the glass wafer 2002 is wet or dry etched. Wet etching is typically quicker, but may lead to isotropic etch profiles.

Figure 22:
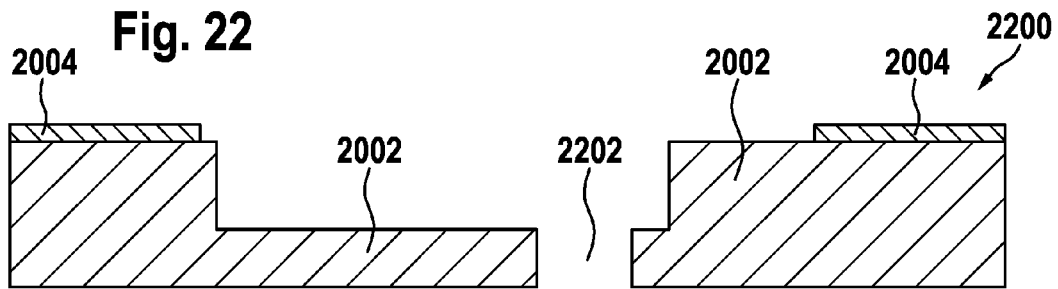

A layer sequence 2200 shown in FIG. 22 may be obtained by power blasting or performing a further wet etch procedure. This may be performed to create a through-hole 2202 in the glass wafer 2002.

Figure 23:
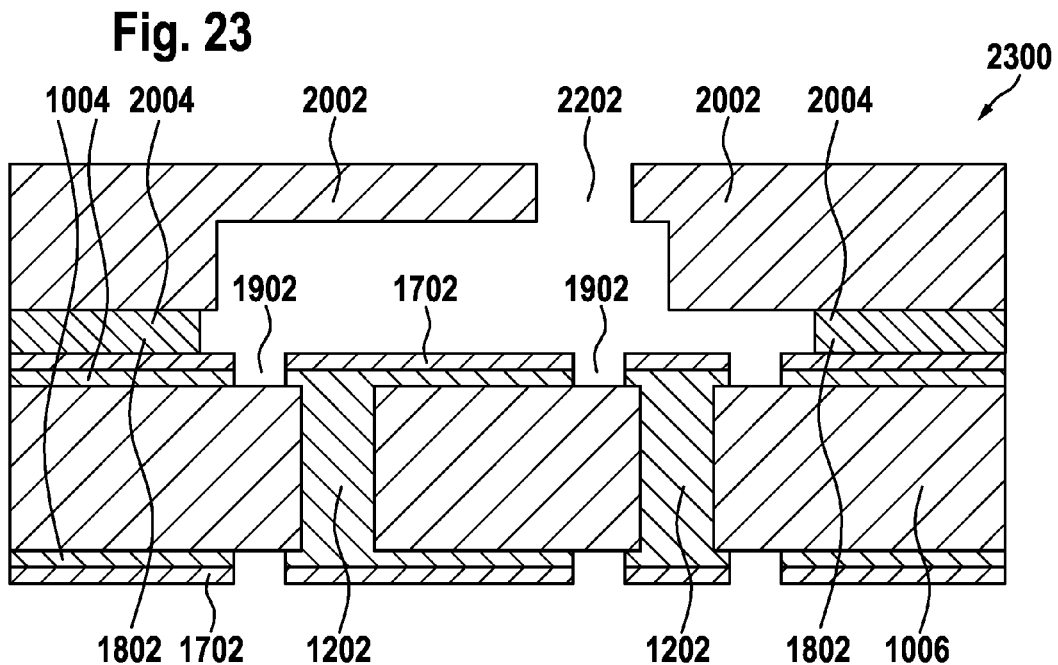

As can be seen as a layer sequence 2300 shown in FIG. 23, the layer sequence 1900 shown in FIG. 19 and the layer sequence 2200 shown in FIG. 22 may be bonded by gold thermo compression.

Figure 24:
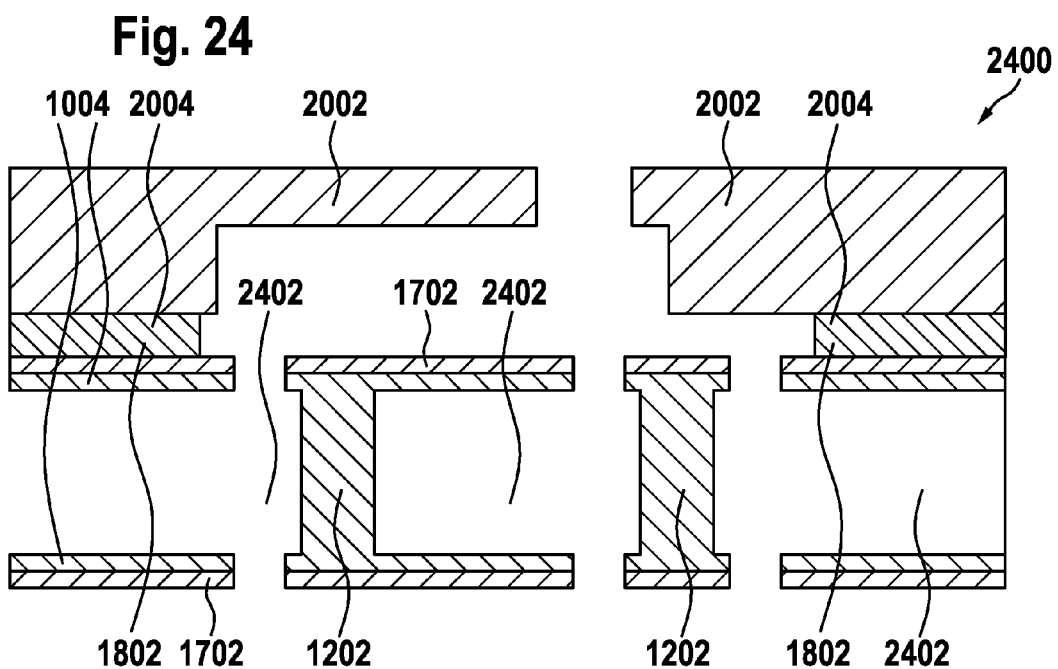

In order to obtain a layer sequence 2400 shown in FIG. 24, silicon material previously denoted with reference numeral 1006 may then be removed. This may create cavities 2402 for the flow cell. For this purpose, a selective silicon etchant may be used to clear out the silicon where required (for instance low pH TMAH or $XeF_2$). This leaves a cell that is only surrounded by silicon oxide material. Silicon may remain in certain areas to provide the frame and additional mechanical support.

Figure 25:
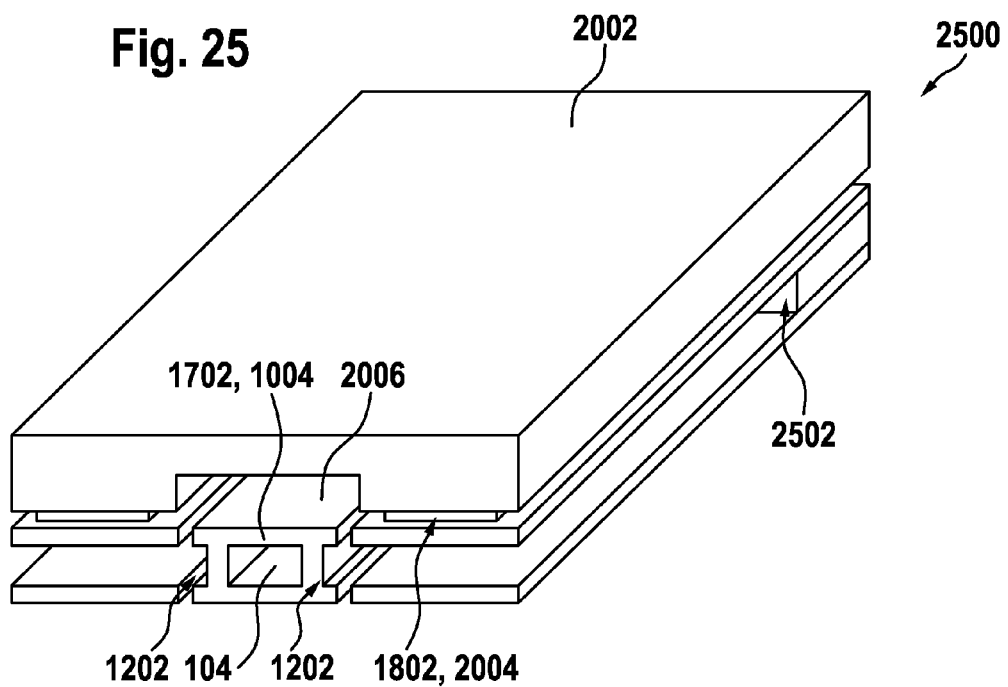
FIG. 25 and FIG. 26 show three-dimensional views of a monolithically integrated flow cell according to an exemplary embodiment.
Figure 26:
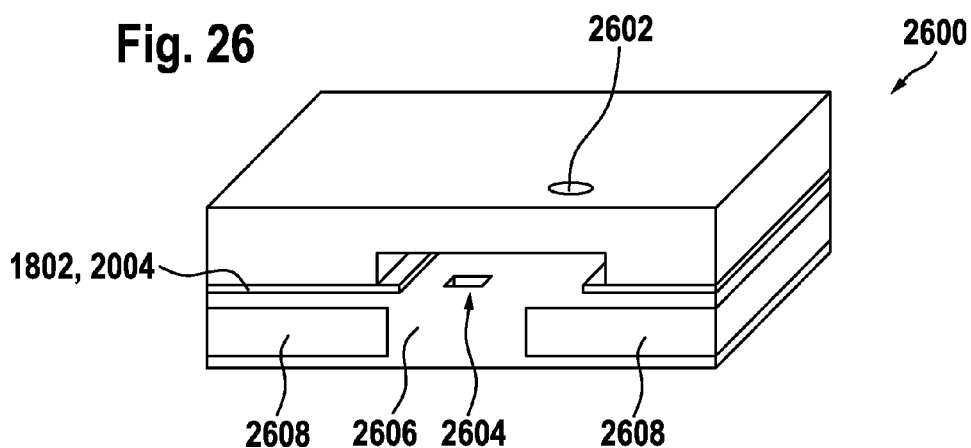

Perspective views are shown in FIG. 25 and FIG. 26.

FIG. 25 shows a three-dimensional view of a flow cell 2500 in which silicon material remaining for mechanical stability is denoted with reference numeral 2502. It does not touch sidewall oxide. Gold for thermo compression is denoted with reference numerals 1802, 2004. The capillary is shown and denoted with reference numeral 104. The sidewall oxide 1202 forms part of the silicon oxide tubing. Trench 2006 in the glass wafer 2002 is shown as well. If desired, a plate 2002 may be additionally attached to the bottom side of the flow cell 2500. FIG. 25 is a three-dimensional view of a segment of a single cell 2500 that can be one of a plurality of cells. The region where liquid is present for analysis (analysis chamber) is surrounded only by thin dielectrics, and this capillary 104 is prestanding in this area. Light may be coupled at the end of the capillary (not shown in FIG. 25). Holes in the roof oxide 1702 to connect to the analysis chamber are not shown, nor are the through holes 2202 in the glass substrate 2002. For a practical layout, the trenches and through holes in the glass may be displaced from the analysis chamber, with only a very narrow trench leading to a hole in the roof oxide.

FIG. 26 shows a three-dimensional view of a flow cell 2600 according to an exemplary embodiment.

FIG. 26 illustrates a cross section near the end of the capillary. A fluid inlet or outlet port 2602 is shown. A via to the cell is denoted with reference numeral 2604. An end of the capillary 2606 is shown as well. Furthermore, a silicon frame 2608 is shown. The trench in the glass is not continuous so that the liquid of interest flows only in the cell 2600 and is not allowed to flow over the roof along the length of the cell 2600. The trench at the end of the cell allows liquid to get from the fluid inlet/outlet port 2602 to the via for the cell 2600. Because some clamping of the capillaries is required, there is a small region where light can couple into the flow cell.

The manufactured quartz capillary (which may serve as a flow cell) may be a mechanically sensitive structure which may be subject to high mechanical stress during use. In order to allow for a use of such a structure even under harsh conditions, stress-reducing measures (for instance flex structures) may be taken.

Figure 27:
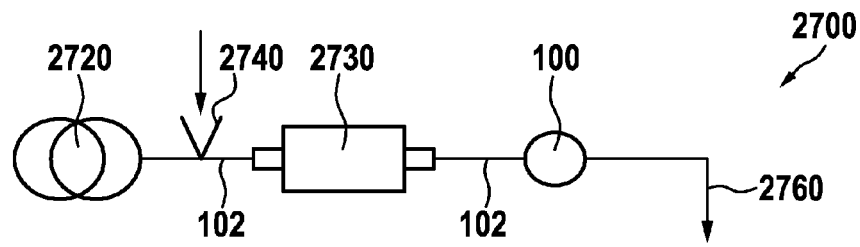
FIG. 27 illustrates a liquid chromatography system according to an exemplary embodiment.

FIG. 27 depicts a general schematic of a liquid separation system 2700. A pump 2720—as a mobile phase drive—drives a mobile phase through a separating device 2730 (such as a chromatographic column) comprising a stationary phase. A sampling unit 2740 can be provided between the pump 2720 and the separating device 2730 in order to introduce a sample fluid to the mobile phase. The stationary phase of the separating device 2730 is adapted for separating compounds of the sample liquid. A detector 100, as the one shown in FIG. 1, is provided for detecting separated compounds of the sample fluid. A fractionating unit 2760 can be provided for outputting separated compounds of sample fluid.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. An integrated flow cell, comprising:
   a semiconductor substrate;
   a fluidic conduit having an at least partially transparent semiconductor oxide tubing formed with the semiconductor substrate and comprising a semiconductor oxide to air transition providing total reflection along a measurement length within the fluidic conduit;
   at least one window element coupling UV-Visible electromagnetic radiation into or out of the fluidic conduit;
   an inlet for supplying a fluidic sample to the fluidic conduit; and
   an outlet for draining the fluidic sample from the fluidic conduit.

2. The flow cell according to claim 1, comprising at least one of:
   the semiconductor substrate is a silicon substrate and the semiconductor oxide tubing is a silicon oxide tubing;
   the semiconductor substrate is a monocrystalline substrate;
   the semiconductor oxide tubing is at least partially embedded in the semiconductor substrate;
   the semiconductor oxide tubing has a rectangular cross section;
   the semiconductor oxide tubing has a hexagonal cross section;
   a surface of the semiconductor oxide tubing is lined with a reflection layer adapted so that a UV-Visible electromagnetic radiation beam propagating through the fluidic conduit is totally reflected at the reflection layer;
   a surface of the semiconductor oxide tubing is lined with a reflection layer adapted so that a UV-Visible electromagnetic radiation beam propagating through the fluidic conduit is totally reflected at the reflection layer, wherein the reflection layer comprises polytetrafluoroethylene;
   an outer surface of the semiconductor oxide tubing is lined with a reflection layer adapted so that a UV-Visible electromagnetic radiation beam propagating through the fluidic conduit is totally reflected at the reflection layer;

the flow cell comprises a plurality of independently operable fluidic conduits each delimited by a semiconductor oxide tubing connected to a common semiconductor substrate;

the flow cell is adapted to conduct a fluidic sample with a high pressure;

the flow cell is adapted to conduct a fluidic sample with a pressure of at least 50 bar, particularly of at least 100 bar, more particularly of at least 500 bar, still more particularly of at least 1000 bar;

the flow cell is adapted to conduct a liquid sample;

the flow cell is adapted as a microfluidic flow cell;

the flow cell is adapted as a nanofluidic flow cell;

the flow cell is a monolithically integrated flow cell, wherein the semiconductor oxide tubing is monolithically formed with the semiconductor substrate.

3. The flow cell according to claim 1, wherein the semiconductor oxide tubing has a tubular section and has a planar section, the tubular section delimiting the fluidic conduit and the planar section defining a beginning and an end of the fluidic conduit in the semiconductor substrate.

4. The flow cell according to claim 1, wherein the semiconductor oxide tubing is optically transparent.

5. The flow cell according to claim 1, wherein the semiconductor oxide tubing is adapted so that a UV-Visible electromagnetic radiation beam propagating through the fluidic conduit is totally reflected at the semiconductor oxide tubing.

6. The flow cell according to claim 1, comprising a UV-Visible electromagnetic radiation source adapted for generating a UV-Visible electromagnetic radiation beam and for coupling the UV-Visible electromagnetic radiation beam into the fluidic conduit.

7. The flow cell according to claim 6, comprising at least one of:

the UV-Visible electromagnetic radiation source is adapted for generating one of an optical light beam and an ultraviolet beam;

the flow cell comprises a UV-Visible electromagnetic radiation detector adapted for detecting the UV-Visible electromagnetic radiation beam after propagation through the fluidic conduit;

the flow cell comprises a UV-Visible electromagnetic radiation detector adapted for detecting the UV-Visible electromagnetic radiation beam after propagation through the fluidic conduit, wherein the UV-Visible electromagnetic radiation detector comprises one of an optical light detector, and an ultraviolet radiation detector.

8. The flow cell according to claim 7, wherein the UV-Visible electromagnetic radiation detector is adapted for receiving the UV-Visible electromagnetic radiation beam from the fluidic conduit via the second window element.

9. The flow cell according to claim 6, comprising at least one of:

the flow cell comprises a first optical coupler element, particularly an optical fiber piece, arranged between the UV-Visible electromagnetic radiation source and the fluidic conduit to couple the UV-Visible electromagnetic radiation from the UV-Visible electromagnetic radiation source into the fluidic conduit;

the flow cell comprises a second optical coupler element, particularly a UV-Visible optical fiber piece, arranged between the fluidic conduit and a UV-Visible electromagnetic radiation detector to couple the UV-Visible electromagnetic radiation from the fluidic conduit into the UV-Visible electromagnetic radiation detector.

10. The flow cell according to claim 1, wherein the at least one window element comprises:

a first window element being transparent to UV-Visible electromagnetic radiation and being located at a first end portion of the fluidic conduit; and a second window element being transparent to UV-Visible electromagnetic radiation and being located at a second end portion of the fluidic conduit opposing the first end portion.

11. The flow cell according to claim 10, wherein the UV-Visible electromagnetic radiation source is adapted for coupling the UV-Visible electromagnetic radiation beam into the fluidic conduit via the first window element.

12. The flow cell according to claim 1, wherein the inlet comprises:

a fluid supply hole formed in the semiconductor oxide tubing for supplying the fluidic sample to the fluidic conduit, 13. The flow cell according to claim 12, comprising at least one of:

the fluid supply hole is adapted for a fluidic connection to a processing element;

the fluid supply hole is also formed in the semiconductor substrate for supplying the fluidic sample to the fluidic conduit.

14. The flow cell according to claim 1, wherein the outlet comprises:

a fluid drain hole formed in the semiconductor oxide tubing for draining the fluidic sample from the fluidic conduit.

15. The flow cell according to claim 14, wherein the fluid drain hole is also formed in the semiconductor substrate for draining the fluidic sample from the fluidic conduit.

16. A fluidic device for measuring a fluidic sample, the fluidic device comprising:

a processing unit adapted for processing the fluidic sample;

a flow cell according to claim 1 in fluid communication with the processing unit for receiving the processed fluidic sample from the processing unit.

17. The fluidic device according to claim 16, comprising at least one of:

the processing element is adapted for retaining the fluidic sample being a part of a mobile phase and for allowing other components of the mobile phase to pass the processing element;

the processing element comprises a separation column;

the processing element comprises a chromatographic column for separating components of the fluidic sample;

at least a part of the processing element is filled with a fluid separating material;

at least a part of the processing element is filled with a fluid separating material, wherein the fluid separating material comprises beads having a size in the range of 1 µm to 50 µm; at least a part of the processing element is filled with a fluid separating material, wherein the fluid separating material comprises beads having pores having a size in the range of 0.02 µm to 0.03 µm;

the flow cell is arranged downstream of the processing unit;

the processing unit comprises a plurality of planar layers laminated to one another;

the processing unit comprising a microstructured body and porous material covering at least a portion of a surface of the microstructured body;

the fluidic device is adapted as a fluid separation system for separating compounds of the fluidic sample;

the fluidic device is adapted to analyze at least one physical, chemical and/or biological parameter of at least one compound of the fluidic sample;

the fluidic device comprises at least one of the group consisting of a sensor device, a test device for testing a device under test or a substance, a device for chemical, biological and/or pharmaceutical analysis, a capillary electrophoresis device, a liquid chromatography device, an HPLC device, a gas chromatography device, and a gel electrophoresis device.

18. A method of manufacturing an integrated flow cell, the method comprising:

providing a semiconductor substrate;

forming a fluidic conduit having an at least partially transparent semiconductor oxide tubing, wherein the semiconductor oxide tubing is formed with the semiconductor substrate and is formed with a semiconductor oxide to air transition providing total reflection along a measurement length within the fluidic conduit;

forming at least one window element coupling UV-Visible electromagnetic radiation into or out of the fluidic conduit;

forming an inlet for supplying a fluidic sample to the fluidic conduit; and forming an outlet for draining the fluidic sample from the fluidic conduit.

19. The method according to claim 18, comprising at least one of:

the method comprises forming the semiconductor oxide tubing by converting a part of the semiconductor substrate from semiconductor material into semiconductor oxide material;

the method comprises forming the semiconductor oxide tubing by thermally annealing a surface of the semiconductor substrate;

the method comprises forming the semiconductor oxide tubing by deposition of semiconductor oxide material on a surface of the semiconductor substrate;

the method comprises patterning the semiconductor substrate before forming the semiconductor oxide tubing;

the method comprises patterning the semiconductor substrate by anisotropic etching of material of the semiconductor substrate before forming the semiconductor oxide tubing;

the method comprises patterning the semiconductor substrate by mechanically weakening a surface portion of the semiconductor substrate and subsequently removing the mechanically weakened surface portion;

the method comprises patterning the semiconductor substrate by mechanically weakening a surface portion of the semiconductor substrate and subsequently removing the mechanically weakened surface portion, wherein the surface portion of the semiconductor substrate is mechanically weakened by forming a comb-shaped structure in the surface portion and by subsequently oxidizing the comb-shaped structure;

the method comprises patterning the semiconductor substrate by anisotropic etching along a plane before forming the semiconductor oxide tubing to thereby form a trapezoidal recess in the semiconductor substrate;

the method comprises patterning the semiconductor substrate by anisotropic etching along a plane before forming the semiconductor oxide tubing to thereby form a trapezoidal recess in the semiconductor substrate, wherein the semiconductor substrate is patterned by the anisotropic etching along the plane so that slanted side walls of the trapezoidal recess correspond to a plane of the semiconductor substrate;

the method comprises forming the semiconductor oxide tubing in a recess of the semiconductor substrate formed by patterning the semiconductor substrate, and bonding two semiconductor substrates both having a semiconductor oxide tubing in a recess in such a manner that the recesses together form the fluidic conduit;

the method comprises forming the semiconductor oxide tubing in a recess of the semiconductor substrate formed by patterning the semiconductor substrate, and bonding two semiconductor substrates both having a semiconductor oxide tubing in a recess in such a manner that the recesses together form the fluidic conduit, further comprising selectively removing a part of the material of at least one of the two semiconductor substrates;

the method comprises forming the semiconductor oxide tubing in a recess of the semiconductor substrate formed by patterning the semiconductor substrate, and bonding two semiconductor substrates both having a semiconductor oxide tubing in a recess in such a manner that the recesses together form the fluidic conduit, further comprising selectively removing a part of the material of at least one of the two semiconductor substrates, wherein selectively removing the part of the material of the at least one of the two semiconductor substrates is performed by etching, particularly by wet etching;

the method comprises forming a cover structure covering an outer surface of the semiconductor oxide tubing, the cover structure having a refraction index being smaller than a refraction index of the semiconductor oxide tubing;

the semiconductor oxide is formed based on the semiconductor.

* * * * *

UNITED STATES PATENT AND TRADEMARK OFFICE
CERTIFICATE OF CORRECTION

| | | |
|---|---|---|
| PATENT NO. | : 8,213,015 B2 | Page 1 of 1 |
| APPLICATION NO. | : 12/237398 | |
| DATED | : July 3, 2012 | |
| INVENTOR(S) | : Karsten Kraiczek et al. | |

It is certified that error appears in the above-identified patent and that said Letters Patent is hereby corrected as shown below:

On the face page, in field (75), in "Inventors", in column 1, line 1, delete "Kraizcek," and insert -- Kraiczek, --, therefor.

In column 18, line 19, in Claim 12, delete "conduit," and insert -- conduit. --, therefor.

Signed and Sealed this
Fourteenth Day of August, 2012

David J. Kappos
*Director of the United States Patent and Trademark Office*